United States Patent [19]

Hlaban

[11] Patent Number: 4,475,913
[45] Date of Patent: Oct. 9, 1984

[54] SANITARY NAPKIN WITH SOFT EDGES

[75] Inventor: James J. Hlaban, Winnebago County, Wis.

[73] Assignee: Kimberly-Clark Corporation, Neenah, Wis.

[21] Appl. No.: 395,236

[22] Filed: Jul. 6, 1982

[51] Int. Cl.³ .............................................. A61F 13/16
[52] U.S. Cl. ................................................. 604/387
[58] Field of Search ............... 604/386, 387, 388, 389, 604/390, 391, 385

[56] References Cited

U.S. PATENT DOCUMENTS

| | | | |
|---|---|---|---|
| 3,595,237 | 7/1971 | Sargent et al. | 604/387 |
| 3,913,580 | 10/1975 | Ginocchio | 604/387 |
| 3,954,107 | 5/1976 | Chesky et al. | 604/385 |
| 4,023,571 | 5/1977 | Comerford et al. | 604/385 |
| 4,337,772 | 7/1982 | Roeder | 604/385 |
| 4,376,440 | 3/1983 | Whitehead et al. | 604/387 |

*Primary Examiner*—John D. Yasko
*Attorney, Agent, or Firm*—Howard Olevsky; R. J. Peters; G. E. Croft

[57] ABSTRACT

A sanitary napkin as provided with an absorbent batt folded along the longitudinal edges to provide a soft surface abutting the wearer's legs. The folded portion of the batt is cut away to produce a cavity on the bottom portion; with the cavity having garment attachment adhesive positioned therein.

8 Claims, 4 Drawing Figures

SANITARY NAPKIN WITH SOFT EDGES

FIELD OF THE INVENTION

The subject invention relates to a sanitary napkin and particularly a sanitary napkin having folded edges.

BACKGROUND OF THE INVENTION

One of the traditional ways of forming a sanitary napkin is to assemble the napkin bottom-side up. A fluid pervious covering material is overlayed with an absorbent batt such as a wood pulp fluff so that the edges of the batt and the cover are coterminous. The absorbent batt is then folded onto itself to produce a double thickness which is wrapped by the fluid pervious cover. Traditionally the fluid impermeable baffle was then added to maintain the fold in place as well as to provide the necessary fluid barrier to the finished napkin. The napkin resulting from this construction has folded longitudinal edges which are soft and comfortable to the wearer.

An example of sanitary napkins made as described above are sold by Kimberly-Clark Corporation, Neenah, Wis. under the trademark ANYDAY.

SUMMARY OF THE INVENTION

According to this invention, a sanitary napkin is provided which has an absorbent batt folded along the longitudinal edges of the napkin. The double thickness obtained by the fold extends only relatively slightly inward leaving a cavity between the doubled over edge portions of the absorbent batt. A fluid impervious baffle is applied which conforms to this configuration and a pressure sensitive garment attachment adhesive is positioned in the cavity. Due to the positioning of the garment attachment adhesive within the cavity, no release liner is needed because of the shielding of the surface of the adhesive by the walls of the cavity.

A substantial savings in material results due to the elimination of a large portion of the bottom layer of the absorbent batt.

DETAILED DESCRIPTION OF THE INVENTION

Figure 1:
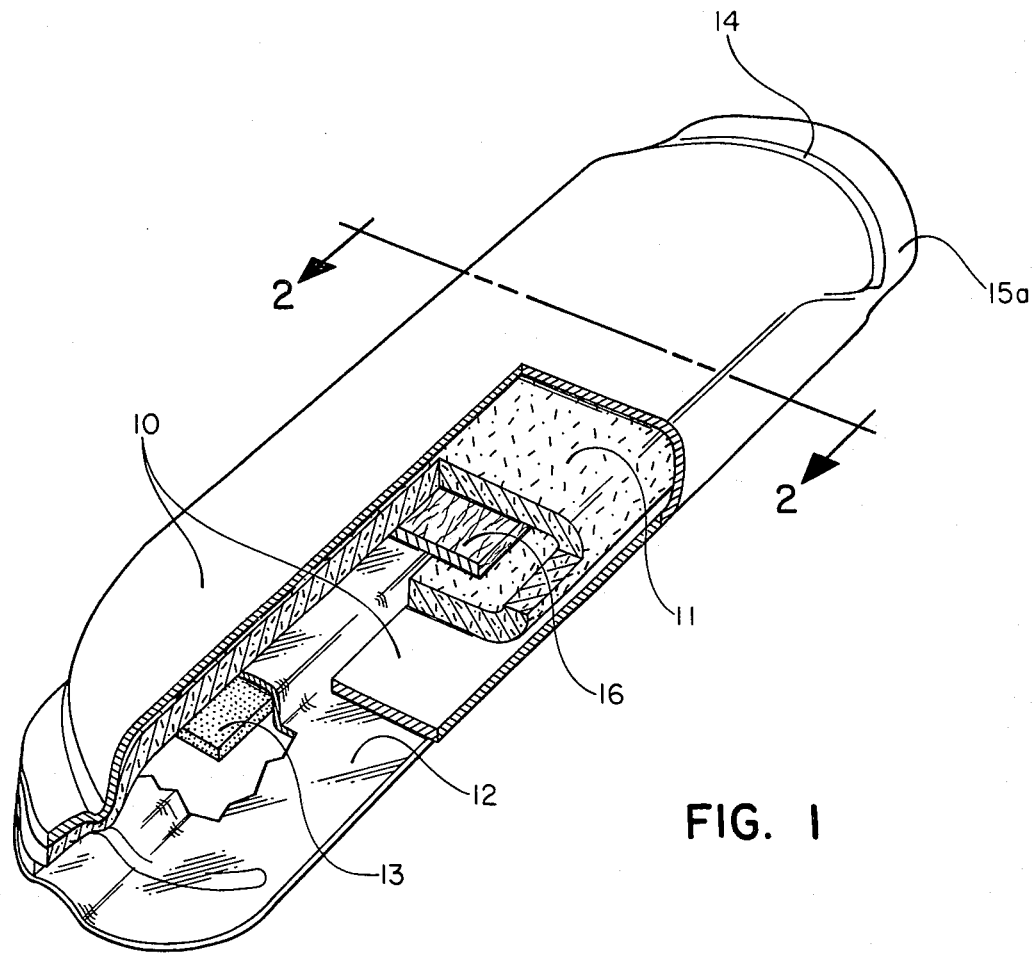
Figure 3:
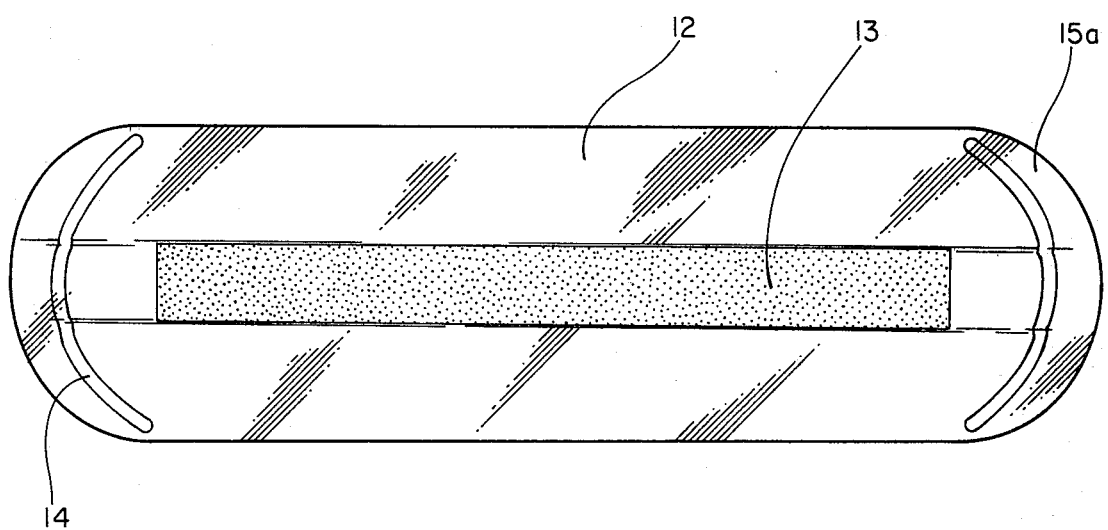
Figure 2:
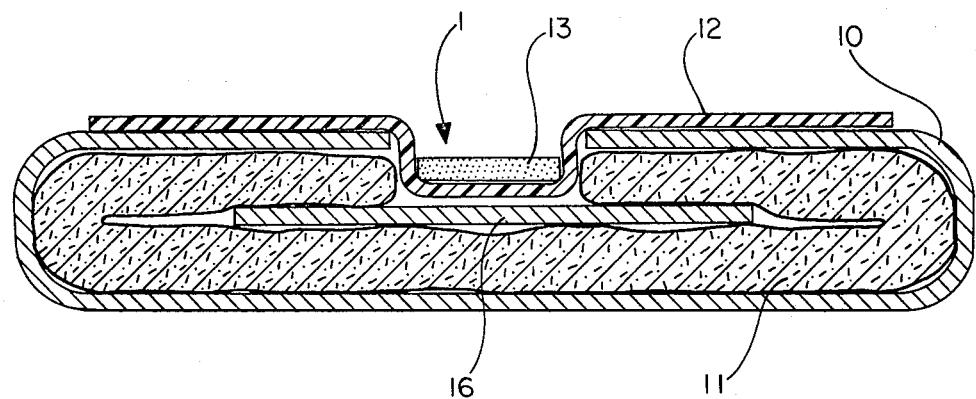
Figure 4:
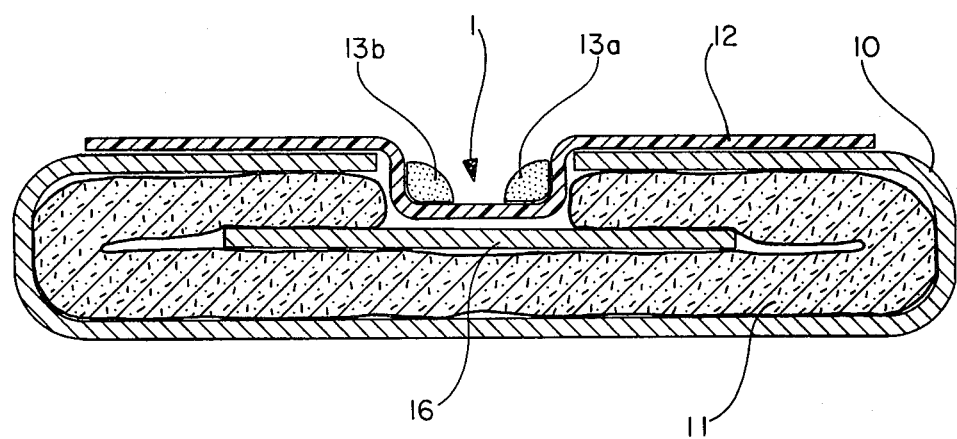

This invention can be more readily understood by reference to the drawings in which FIG. 1 is a top plan view partially in cross section of a sanitary napkin made in accordance with the teachings of this invention;

FIG. 2 is a transverse cross-section taken along the lines 2—2 of FIG. 1 of one of the embodiments of this invention, FIG. 3 is a bottom plan view of the embodiment depicted in FIG. 2 and FIG. 4 is a longitudinal cross-section of the second embodiment of the teachings of this invention.

As can be seen from FIGS. 1 and 2, an absorbent batt 11 is overlayed with a fluid permeable wrap 10 which is folded over along the longitudinal edges of the napkin providing a cavity 1 as shown in FIGS. 2 and 4. This configuration is overlaid with a conforming fluid impervious baffle 12. The baffle is applied in fluid form and preferably by extrusion so that the shape conformance and attachment to the bottom of the napkin can be closely controlled. The cavity 1 has a wide band of pressure sensitive adhesive 13 as can be seen in FIGS. 2 and 3 extending along the length of the cavity. As indicated in FIG. 3 the adhesive will desirably terminate prior to the extreme ends of the napkin, although this is not a requirement. The absorbent batt 11 which may contain fusible fibers is sealed at either end as shown by band 14. This sealing may be by adhesive or, if fusible fibers are present, by ultrasonic means as is well known in the art. The extreme upper and lower ends 15a and 15b respectively are flexible because of the compression associated with the seal line 14.

The presence of fusible thermoplastic fibers is desirable because of the additional resiliency resulting from the inclusion of these fibers. For purposes of this invention, a particularly preferred absorbent batt is described in U.S. Pat. No. 4,100,324. The absorbent batt described therein is a nonwoven material with a fabric-like finish and is made of an air formed matrix of thermoplastic polymeric fibers having an average diameter of less than about 10 microns, and a multiplicity of individualized wood pulp fibers dispersed through the matrix which serve to space these microfibers from each other. The material is formed by initially utilizing a primary air stream with the meltblown microfibers and the secondary air stream containing wood pulp fibers and merging the two under turbulent conditions. The integrated air stream then deposits these mixed fibers along a forming surface.

As shown in FIGS. 3 and 4 a strip of absorbent enhancement material 16 such as super absorbent material is positioned within the upper layer of the above absorbent batt for reasons explained earlier. It is possible to place the superabsorbent strip under this upper layer prior to the extrusion coating of the fluid pervious baffle and such positioning is contemplated within the scope of this invention.

The cavity depicted at FIGS. 2 and 4 is generally not greater than about 60% of the area of the bottom of the napkin. The maximum area of the cavity is determined by the necessary amount of absorbent batt which must be folded over to provide the soft edge. If the cavity was larger it would be extremely difficult to obtain the double thickness at the longitudinal edges of the napkin.

Generally the absorbent batt is between 0.2 and 0.5 inches thickness and, as a consequence, the resulting napkin is thin, flexible, conformable, comfortable and with the presence of absorbent additives has a sufficient absorbent capacity for overall menstrual use.

FIG. 4 depicts an alternate adhesive configuration. While this particular configuration consisting of two lines of adhesive 13a and 13b are somewhat more difficult to apply, the adhesive attachment of the napkin due to the two-line positioning and the subsequent release from the undergarment from this particular configuration is superior to the single wide line configuration depicted in FIGS. 2 and 3.

What is claimed is:

1. A sanitary napkin comprising an absorbent batt, a fluid pervious cover coterminous with said batt, said batt folded over along its longitudinal sides to provide a double thickness at the bottom of each side portion; said double thickness portions spaced from each other defining a centrally located cavity, a fluid impervious baffle extending at least over said cavity and comforming thereto and said bottom side portions; and in intimate contact therewith and a pressure sensitive adhesive pattern positioned within said cavity.

2. A sanitary napkin according to claim 1 wherein said cavity is not greater than about 60% of the area of said bottom.

3. The sanitary napkin according to claim 1 or 2 wherein the absorbent batt contains thermoplastic fibers.

4. The sanitary napkin according to claim 1, 2, or 3 wherein the absorbent batt is an air laid blend of wood pulp fiber and thermoplastic microfibers.

5. The sanitary napkin according to claim 1, 2, or 3 wherein the thickness of the absorbent batt is between 0.2 and 0.5 inches.

6. The sanitary napkin according to claim 1, 2, or 3 wherein the cavity has a layer of adhesive extending under the absorbent batt but terminating prior to the ends of the napkin.

7. The sanitary napkin according to claim 1 wherein an absorbent additive is present.

8. A sanitary napkin comprising an absorbent batt, a fluid pervious cover coterminous with said batt, said batt folded over along its longitudinal sides to provide a double thickness at the bottom of each side portion; said double thickness portions spaced from each other defining a centrally located cavity, a fluid impervious baffle extending at least over said cavity and conforming thereto and said bottom side portions; and in intimate contact therewith and two adhesive strips with each strip abutting the bottom edge of the folded, baffle-covered absorbent.

* * * * *

UNITED STATES PATENT AND TRADEMARK OFFICE
CERTIFICATE OF CORRECTION

PATENT NO. : 4,475,913
DATED : October 9, 1984
INVENTOR(S) : James J. Hlaban

It is certified that error appears in the above–identified patent and that said Letters Patent are hereby corrected as shown below:

At line 7 of Claim 1 change "comforming" to --conforming--.

Signed and Sealed this

Sixteenth Day of April 1985

[SEAL]

Attest:

DONALD J. QUIGG

Attesting Officer    Acting Commissioner of Patents and Trademarks